United States Patent [19]

Nappholz et al.

[11] Patent Number: 5,312,445
[45] Date of Patent: May 17, 1994

[54] IMPLANTABLE CARDIAC STIMULATING APPARATUS AND METHOD EMPLOYING DETECTION OF P-WAVES FROM SIGNALS SENSED IN THE VENTRICLE

[75] Inventors: Tibor A. Nappholz, Englewood; Saul E. Greenhut, Aurora; Albert K. Dawson, Denver, all of Colo.

[73] Assignee: Telectronics Pacing Systems, Inc., Lane Cove, Australia

[21] Appl. No.: 830,395

[22] Filed: Feb. 3, 1992

[51] Int. Cl.$^5$ .................................. A61N 1/362
[52] U.S. Cl. ........................................... 607/9
[58] Field of Search .............. 128/419 PG; 607/9, 17

[56] References Cited

U.S. PATENT DOCUMENTS

| | | | |
|---|---|---|---|
| 4,298,007 | 11/1981 | Wright et al. | 128/429 PG |
| 4,313,442 | 2/1982 | Knudson et al. | 128/419 PG |
| 4,515,161 | 5/1985 | Wittkampf et al. | 128/419 PG |
| 4,535,776 | 8/1985 | Strandberg et al. | 128/419 PG |
| 4,543,963 | 10/1985 | Gessman | 128/419 PG |
| 4,779,617 | 10/1888 | Whigham | 128/419 P |
| 4,821,724 | 4/1989 | Whigham et al. | 128/419 P |
| 4,901,725 | 2/1990 | Nappholz et al. | 128/419 PG |
| 4,905,696 | 3/1990 | Amundson et al. | 128/419 PG |
| 4,913,146 | 4/1990 | DuCote Jr. | 128/149 PG |
| 4,940,052 | 7/1990 | Mann et al. | 128/419 PG |
| 5,078,133 | 1/1990 | Heinze et al,. | 128/419 PG |

OTHER PUBLICATIONS

J. C. Pitts Crick, "European Multicenter Prospective Follow-Up Study of 1,002 Implants of a Single Lead VDD Pacing Systems", *PACE*, vol. 14, pp. 1742–1744 (Nov. 1991, Part II).

*Primary Examiner*—William E. Kamm
*Attorney, Agent, or Firm*—Gottlieb, Rackman and Reisman

[57] ABSTRACT

A P-wave detector in a single chamber ventricular cardiac pacemaker, which is adapted to perform VDD pacing, senses natural atrial activity in the form of P-waves from a standard lead implanted in the ventricle of the heart. The P-wave detector is electrically coupled to a ventricular sensing lead and, although the electrode of the lead is implanted in the ventricle, circuitry within the pacemaker perceives intrinsic cardiac electrical activity arising from all parts of the heart. The P-wave detector is adapted to differentiate P-wave signals arising within the atrium from other cardiac and non-cardiac signals using template matching techniques in which an acquired signal is compared with a previously stored P-wave template.

21 Claims, 5 Drawing Sheets

IMPLANTABLE CARDIAC STIMULATING APPARATUS AND METHOD EMPLOYING DETECTION OF P-WAVES FROM SIGNALS SENSED IN THE VENTRICLE

TECHNICAL FIELD

This invention relates generally to cardiac pacemakers having a single lead implanted within the ventricle of the heart for stimulating heartbeats and sensing cardiac electrical signals, and more particularly to such pacemakers which analyze such cardiac electrical signals to distinguish atrial depolarizations (P-waves) arising remote from the ventricle, for the purpose of controlling ventricular stimulation timing.

BACKGROUND OF THE INVENTION

In the heart, natural atrial electrical depolarization waves propagate from the sinus node through the atrium to the atrioventricular node to stimulate the ventricle. In some diseased hearts, the electrical conduction pathway breaks down, so that the sinus node triggers the electrical heartbeat process but the electrical impulse does not conduct to the ventricle.

Dual-chamber pacemakers adapt pacing rate and timing to a patient's needs by sensing natural atrial heartbeat signals (P-waves) and by generating electrical stimulating pulses in the ventricle in response to the timing of sensed P-waves. The ideal sensor for determining a proper pacing rate is a normally functioning sinus node. Physiologic pacemakers which employ atrial sensing in VDD and DDD pacing modes, as are standard in the art of pacemakers, are truly rate responsive. Dual-chamber pacing is an effective therapy for high degree atrioventricular block, particularly for patients in which the natural sinus (rate-determining) mechanism is intact and functioning normally. In such cases, the rate-determining response of the pacemaker to emotion or exertion is the same as that of the normal heart's rate-setting mechanisms. Thus, the pacemaker acts as an artificial atrioventricular conducting system to reestablish A-V synchrony.

One disadvantage of a standard dual-chamber pacemaker is that it requires implantation of an atrial lead. An atrial lead presents multiple technical problems which arise from the anatomical and physiological nature of the atrium. The atrial wall is much thinner than the ventricular wall. Implanting a lead in the atrium is more likely to injure cardiac tissue, leading to difficulties in sensing natural atrial signals and possibly causing tissue scarring, resulting in dangerous arrhythmia conditions.

A ventricular lead can hold its electrode position with more stability than can an atrial lead. Leads are difficult to "fix" within atrial tissue in a stable position which is conducive to effective cardiac signal sensing. An atrial electrode which is not firmly affixed may cause intermittent P-wave sensing.

Pacing the atrial chamber is difficult due to the difficulty in affixing the atrial electrode to the thin atrial tissue. Furthermore, atrial stimulation may induce atrial arrhythmias such as atrial fibrillation.

Furthermore, the requirement for two leads in standard dual-chamber pacemakers leads to an increase in logical complexity, intensifying the dangers of improper interactions between control operations involved in pacing the two chambers, due to errors in programming variables which control the pacing interaction and the occurrence of unforeseen physiological events which disrupt the control pattern between the two heart chambers. With two leads, twice the danger of injury to heart tissue exists. Furthermore, a dual lead system is inherently more expensive than a single lead pacemaker.

Excessive current drain is an additional disadvantage of dual-lead pacemakers. In addition, a single lead pacemaker is much preferable for patients having a small vein diameter, such as children.

One manner of addressing the disadvantages of standard dual-chamber pacing was to perform single-chamber pacing in the ventricle (VVI) while including an extra sensor in the ventricle which did not generate atrial stimulation pulses, but merely sensed atrial cardiac activity. Knudson et al. in U.S. Pat. No. 4,313,442, entitled "Atrial Rate Sensitive Cardiac Pacer Apparatus", issued Feb. 2, 1982, described a pacemaker with a single lead implanted in the ventricle of the heart which sensed cardiac atrial signals to determine cardiac demand and altered cardiac output to satisfy that demand. The lead had an electrode at its distal end implanted in the ventricle of the heart for sensing ventricular cardiac electrical signals and for stimulating ventricular pacing pulses. In addition, the lead had a second electrode located proximal to the first in a manner such that it was situated within the atrium of the heart. The second electrode sensed cardiac electrical signals arising from the atrium. Changes in atrial electrical cycle intervals were detected and averaged over multiple cardiac cycles to provide a control signal which was used to modulate the ventricular heart rate and, consequently, cardiac output. Wright et al. in U.S. Pat. No. 4,298,007, entitled "Atrial Rate Sensitive Cardiac Pacer Circuit", issued Nov. 3, 1981, described a circuit which performed the operations designated in the Knudson et al. patent. In this pacemaker, the lead was capable of sensing atrial depolarization, but atrial pacing was not possible since the electrode was not in contact with the atrial wall.

A number of problems arose in the Knudson et al. and Wright et al. systems. First, implantation of the ventricular electrode involved critical logistic problems. The ventricular electrode required implantation such that the atrial electrode was positioned where it could properly sense atrial depolarizations. A physician needed to implant the ventricular electrode, then test the atrial electrode for positioning and atrial signal sensing. If the position was not correct, the physician was required to remove the lead and attempt a second lead implantation using a lead with a different distance between the atrial and ventricular electrodes. Changing the leads was extremely difficult. Using subclavian punctures, a large introducing cannula (in situ) was required to confirm the occurrence of adequate atrial sensing. This implantation procedure was extremely difficult, cumbersome, prolonged and expensive. Furthermore, after the operation, atrial sensing was not always reliable and P-wave amplitudes were often inadequate.

A second problem with the Knudson et al. and Wright e al. pacemakers was that, in contrast to single chamber ventricular pacemakers, they required a special lead with separate electrodes for the atrium and the ventricle. A major disadvantage of the lead was its large size which was necessary to enclose three conductors. This lead was not standard for cardiac pacing and required additional electronics within the pacemaker which may increase the size and energy requirements of the electronics within the pacemaker, leading to an increased pacemaker size or a decreased service lifetime. Furthermore, it was often desirable to implant a new pacemaker and attach it to previously implanted leads. The Knudson et al. and Wright et al. pacemakers could not be attached to leads other than the required special leads.

A third problem with the Knudson et al. and Wright et al. pacemakers was that the atrial lead was free-floating in the atrial chamber of the heart, leading to inconsistent sensing of atrial signals.

A fourth problem existed in the Knudson et al. and Wright et al. pacemakers. Because sensing was not reliable, the pacemakers did not provide for P-waves to trigger ventricular pacing, but instead P-wave intervals were detected and averaged to determine the ventricular pacing rate. The pacemakers did not perform synchronous pacing so, unlike the result of a pacemaker operating in VDD or DDD pacing mode, there was no boost to cardiac hemodynamic output. The pacemakers were not as efficient as conventional DDD pacemakers.

J.C.P. Crick in "European Multicenter Prospective Follow-Up Study of 1,002 Implants of a Single Lead VDD Pacing System", PACE. Vol. 14, pages 1742-1744 (1991), discusses a pacemaker which solves the fourth stated problem afflicting the Knudson et al. and Wright et al. system by providing for sensing of P-waves and triggering of ventricular pacing pulse generation. However, the pacemaker discussed by Crick does require a special pacing lead which includes an electrode which is implanted within the atrium, the second stated disadvantage of the Knudson et al. and Wright et al. pacemakers.

When a heart's natural sinus mechanism is not operating properly, a ventricular rate responsive pacemaker may better provide for physiological rate-determination than a DDD pacemaker. However, an important limitation of rate responsive ventricular pacing arises upon the occurrence of retrograde conduction, wherein a depolarizing impulse from the ventricular myocardium is transmitted to the atrial myocardium, possibly triggering dangerous ventricular arrhythmias or generating cannon A-waves. Cannon A-waves are large abrupt waves in the jugular venous pulse that occur when the respectively contract against a closed tricuspid valve and a closed bicuspid valve due to atrioventricular asynchrony or ventricular tachycardia. For patients suffering from retrograde conduction, the addition of a sensor to increase pacing rate with exercise will not improve the cardiac output but rather will depress it even further. Therefore, the implantation of a ventricular rate responsive pacemaker may be contraindicated in some of the patients for whom it has been specifically designed, patients with the sick sinus syndrome and chronotropic dysfunction but who have intact ventriculo-atrial conduction.

BRIEF SUMMARY OF THE INVENTION

An ideal pacing sensor is a heart's normally functioning sinus node. Physiologic pacing systems using atrial sensing (VDD, DDD) are truly rate responsive. The present invention is a pacemaker which is capable of performing VDD pacing (atrial-synchronized, ventricular-inhibited pacing) employing a single lead implanted in the ventricle of the heart. This lead is most commonly a unipolar or bipolar ventricular lead which is standard in the art of cardiac pacing. Although the atrial signal, which is detected from an electrode implanted within the ventricle by the pacemaker of the present invention, does not have the fidelity of such a signal detected on an atrial lead, sophisticated signal processing techniques provide for efficient detection of P-waves.

In accordance with the principles of the present invention, a single chamber ventricular cardiac pacemaker is adapted to perform VDD pacing by sensing natural atrial activity, in the form of P-waves, from a lead implanted in the ventricle of the heart and which lead includes at least one electrode. Normally, the pacemaker of the present invention is coupled with a standard unipolar (single-electrode) or a standard bipolar (dual-electrode) lead. Each electrode is implanted in the ventricle of the heart and is electrically coupled to a sensing means and a pulse generating means. The sensing means is adapted for sensing intrinsic cardiac electrical activity arising from heart tissue in general, including the atrium as well as the ventricle. Although the pacemaker may sense cardiac electrical activity from the tip electrode of a unipolar lead or from either the tip or ring electrode of a bipolar lead, the preferred embodiment of the pacemaker senses cardiac electrical activity to detect P-waves from the ring electrode of a bipolar lead. The sensing means is coupled to a P-wave detecting means which is adapted to process the sensed signal to differentiate P-wave signals arising from the atrium from other cardiac signals, including signals which arise within the ventricle. The pulse generating means is adapted to initiate and deliver pacing stimulation pulses to an electrode to stimulate the ventricle of the heart. The pacemaker further includes a control means with an associated timer for controlling the pulse generating means to stimulate the ventricle based on the timing of at least one detected P-wave.

In accordance with the principles of further aspects of the present invention, the aforementioned P-wave detecting means is adapted to distinguish P-wave signals arising from the atrium from other cardiac signals. The pacemaker determines and stores a template signal which defines the structure of a P-wave signal, then samples cardiac signals and performs a template matching operation to determine whether and when a sampled signal matches the P-wave template. Such matching, to a predetermined degree, defines the occurrence of a P-wave. The first operation of the invention is performed by a template selecting means which is adapted to sample and digitize a P-wave waveform from signals sampled when a P-wave was known to be occurring in the atrium. The template selecting means includes a means for characterizing and storing the P-wave waveform in a time sequence of template samples. Subsequent to selecting the template, when it is not known whether atrial activity in the form of P-waves is occurring, the P-wave detector includes a monitoring means for sampling and digitizing intrinsic cardiac electrical signal samples from the ventricular-implanted electrode. The P-wave detector also includes a template matching means for comparing current digitized samples with the previously stored P-wave template to derive a template matching coefficient and a means for comparing this coefficient with predetermined threshold criteria and classifying current samples as a P-wave when the coefficient meets these criteria.

The present invention provides the advantages of dualchamber pacing in a pacemaker which requires the implantation of only a single standard lead within the ventricle of the heart. Thus implanting two leads through narrow veins with an electrode affixed into thin atrial tissue is not required. Most importantly, the invention provides for atrioventricular synchronous pacing which allows the atrium, during atrial systole, to assist ventricular filling prior to ventricular systole. This increases the cardiac hemodynamic output of a patient at rest by 15-20%. In addition, the pacemaker of this invention performs rate responsive cardiac pacing via monitoring of the frequency of atrial depolarizations to alter the rate of ventricular systole according to physiologic needs in an apparatus which does not require the implantation of an atrial lead. Furthermore, atrioventricular synchronous pacing eliminates pacemaker syndrome, the adverse hemodynamic effects arising from retrograde conduction.

The present invention detects P-waves by sensing and analyzing atrial signals measured from an intracardiac lead implanted within the ventricle of the heart. More particularly, it performs analysis for P-wave detection using template matching techniques.

In accordance with the principles of still further aspects of the present invention, a pacemaker determines an appropriate pacing rate in two ways, using a metabolic indicator sensor and the aforementioned P-wave detecting means. One such metabolic indicator sensor measures respiratory minute volume and, from this measurement, determines a pacing rate which is suitable when the patient is exercising or under stress. An example of such a sensor is shown by Nappholz et al in U.S. Pat. No. 4,702,253, issued Oct. 27, 1987, and entitled "Metabolic-Demand Pacemaker and Method of Using ht Same to Determine Minute volume. The P-wave detecting means is adapted to distinguish P-wave signals arising from the atrium from other cardiac signals. The pacemaker determines and stores a template signal which defines the structure of a P-wave signal, then samples cardiac signals and performs a template matching operation to determine whether and when a sampled signal matches the P-wave template. Such matching, to a predetermined degree, defines the occurrence of a P-wave. If the pacemaker detects P-waves occurring at a rate faster than a predetermined maximum atrial tracking rate, P-wave detection may become less reliable since the P-waves are more likely to occur at the same time as the T-waves arising from ventricular repolarization. Furthermore, at higher rates the morphology of P-waves may change. In addition, high P-wave rates may indicate the occurrence of an arrhythmia condition. Therefore pacing at this rate is assumed to be inappropriate and the pacemaker will deliver pacing stimuli at the metabolic indicator rate, asynchronously with respect to the P-waves. When the pacemaker detects P-waves which occur at a rate slower than the maximum atrial tracking rate, it triggers ventricular pacing stimuli following the A-V delay in synchrony with the detected P-waves.

DETAILED DESCRIPTION

The present invention is a pacemaker which is capable of performing VDD pacing (atrial-synchronized, ventricularinhibited pacing mode), a synchronous pacing mode in which the pacemaker delivers stimulation pulses only in the ventricle of the heart, but the pacemaker senses natural electrical activity in both the atrium and ventricle. Such a pacemaking operation creates a dual mode of response; sensed atrial events trigger ventricular stimulation while sensed ventricular events inhibit the delivery of ventricular stimulation pulses.

Figure 1:
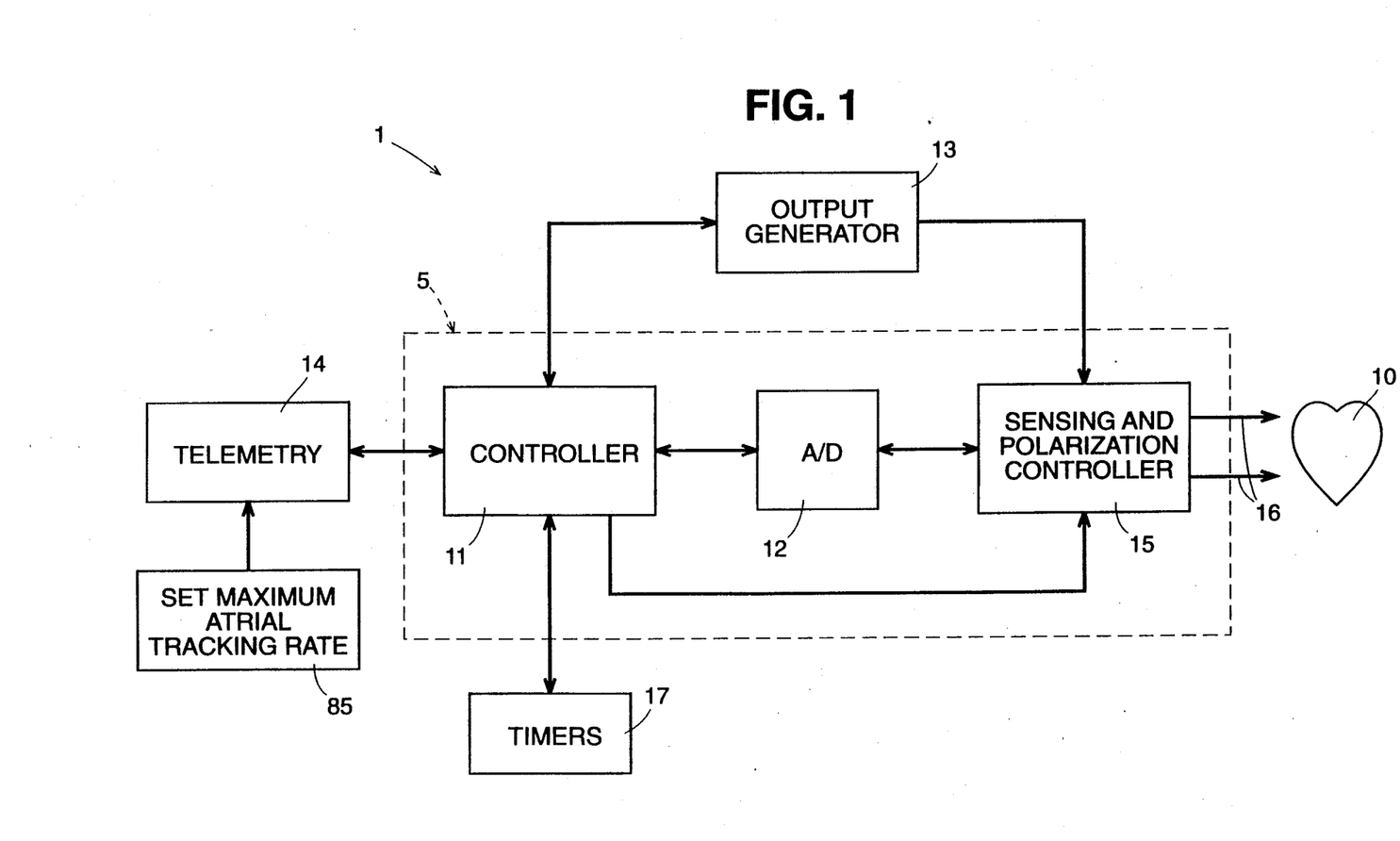
FIG. 1 is a high-level block schematic which illustrates important functional blocks of a preferred embodiment of the invention as utilized in a VDD pacemaker which employs atrial sensing via a ventricular lead P-wave detector.

Referring to FIG. 1, a pacemaker, shown generally at 1, is coupled to a patient's heart 10 via a conventional bipolar lead 16 that is provided with conventional tip and ring electrodes (not shown). The fundamental requirements for pacemaker 1 include the ability to generate and deliver to the heart 10, at selected intervals, electrical stimulation pulses of varying amplitudes and forms.

All pacemaker 1 logic is under the control of controller 11 (which may include a microprocessor), which controls all of the other blocks of FIG. 1. In particular, the controller determines the amplitude and shape of the stimulating pulses and also sets the timing of pulse delivery. The controller also governs the timing and number of acquisitions of intracardiac electrogram samples in addition to determining and executing any signal filtering required for signal analysis. As the controller performs signal sampling, it carries out the analysis necessary for the diagnostic purposes of the device, as described below.

A telemetry block 14 is conventional in modern implanted cardiac pacemakers and defibrillators. It allows for communication of information between an external (not implanted) programming device (not shown) and the pacemaker 1, which permits both the adjustment of the data acquisition parameters from the external device and the transmission of information from the implanted pacemaker to the external device. The information transmitted from the pacemaker 1 to the external device includes accumulated data and a signal representative of the instantaneous sensed intracardiac electrogram. Present-day sophisticated telemetry circuits allow for the interrogation of stored diagnostic data and the derivation of real-time operational data.

The pacemaker 1 uses a form of delta modulation to produce a digital signal for analysis by the controller 11. An analog-to-digital block 12 is provided with a signal called ANGL__CMP from a sensing and polarization controller 15. The ANGL__CMP signal is a two level waveform representing the sensed signal as a sequence of bits indicating the time history of increases and decreases in the signal amplitude. The analog-to-digital block 12 converts the bit sequence into a form which the controller can read to perform the functions of sensing and intracardiac electrogram acquisition. The output signal of the analog-to-digital block 12 tracks the input signal in the sense that the output represents a 1 value when the input is increasing and a 0 value when the input is decreasing.

The controller 11 has a direct connection which controls the sensing and polarization controller 15. The sensing and polarization controller includes control circuits for performing data acquisition and pulse generation. To control sensing sensitivity (or gain), the controller 11 writes commands into the sensing and polarization controller to adjust an 8-bit register (not shown) which, in turn, sets each of eight switches within a resistor network circuit (not shown) to an open or closed condition.

Control words written from the controller 11 to the sensing and polarization controller 15 determine the configuration of its sensing and stimulation circuits. The pacemaker 1 delivers a negative polarity stimulus through that conductor of lead 16 which has an electrical connection to the tip electrode of the lead. Other electrical connections of pacemaker 1 are its case (the electrical connection is with the exterior case of the pacemaker) and the ring electrode of lead 16. When connected in a unipolar mode, the active electrode is at the lead tip, which is in contact with the cardiac tissue to be stimulated, and the indifferent electrode is the case of the implanted pacemaker. When connected in a bipolar mode, the indifferent electrode can be either the case or the ring electrode, which is an annular electrode on the lead a short distance from the tip electrode. A command code written by the controller 11 determines the settings of switches (not shown) to determine which electrode is active and which is indifferent during stimulation as well as sensing. The code may specify a different switch setting during stimulation as compared to sensing. Switch settings determine the operative configuration of the pacemaker: bipolar, unipolar tip-case or unipolar ring-case. Unipolar signals, arising from cardiac potentials accumulated over a larger surface of the ventricle, generally contain more information than bipolar signals, thereby providing a more reliable diagnostic result. On the other hand, bipolar signals offer better rejection of noise, including muscle and motion artifacts, and provide the most detailed signal description of the electrophysiological state from a localized region of the ventricle. Control bytes written by the controller 11 to the sensing and polarization controller 15 determine the setting of other switches to accomplish the tasks of various modes of stimulation and sensor measurement acquisition. These switch settings are described in detail in U.S. Pat. No. 4,821,724 to R. H. Whigham et al., entitled "Pacing Pulse Compensation", issued Apr. 18, 1989, the disclosure of which is incorporated herein by reference.

The pacemaker 1 of the present invention senses cardiac electrical signals from an electrode implanted in the patient's ventricle for the purpose of detecting P-wave atrial depolarizations. An electrode for sensing P-waves is intended to include a tip electrode in the case of a unipolar lead and to include either a tip or ring electrode in the case of a bipolar lead. The preferred embodiment of the pacemaker employs sensing from the ring electrode of a bipolar lead to provide ring-to-case sensing which detects large atrial depolarization signals for most efficient P-wave detection.

An output generator 13, in response to control bytes written by the controller 11, prepares for stimulation by storing electrical charge on capacitors (not shown) and delivers the stimulating pulses, as described in said U.S. Pat. No. 4,821,724. Control bytes written to the output generator by the controller 11 determine the amplitudes, polarities and durations of the phases of the pacing stimulus pulses.

The controller 11 writes timing initialization and duration information to a timer 17. The timer 17 responds to the receipt of this information by generating wake-up signals to the controller after a time interval expires This time interval is determined by the initialization and duration codes written to the timer 17. The controller uses timer wake-ups to govern the timing of cardiac cycles as well as to time short-term intervals for miscellaneous operations, including the setting of timing for intracardiac electrogram sampling. In addition, the controller uses timer wake-up signals to control a real-time clock function for determining the length of time since manufacture of the device and for initiating long-term housekeeping functions.

Figure 2:
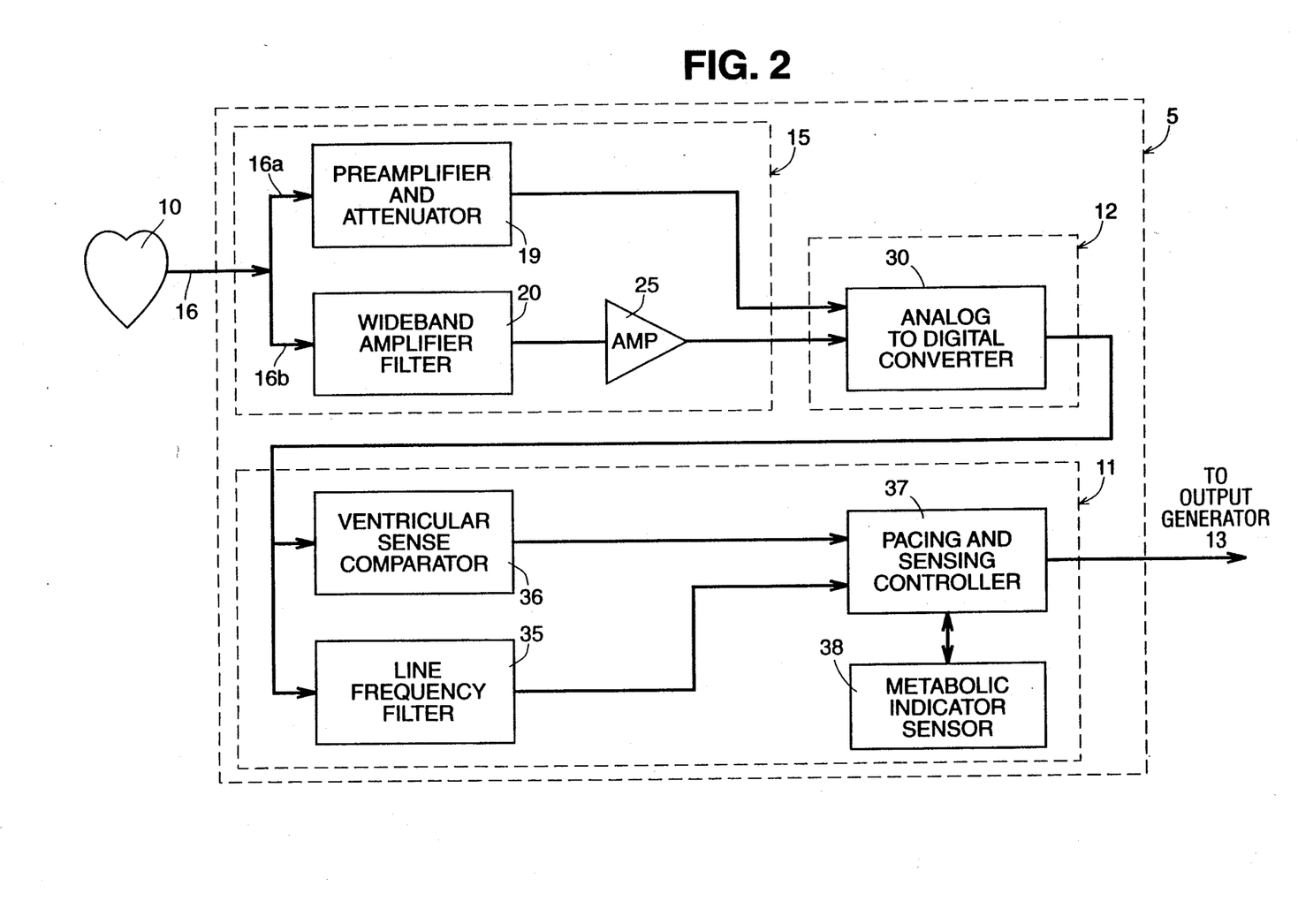
FIG. 2 is a highly schematic block diagram which illustrates the functional elements of a ventricular P-wave detector.

FIG. 2 is a highly schematic block diagram which illustrates a preferred embodiment of a ventricular lead, P-wave detector, shown generally at 5, in accordance with the present invention. This figure exemplifies the usage of the P-wave detector as a cardiac signal analysis element in a cardiac pacemaker adapted to operate in a VDD pacing mode. Heart beat signals are sensed by electrodes (not shown) implanted within the ventricle of the heart 10. The electrodes are electrically connected to leads 16 which extend to signal analysis electronics, including a controller 11 which may be a microprocessor. The P-wave detector 5 detects cardiac signals using one of the standard configurations in cardiac pacing: bipolar, unipolar tip-case or unipolar ring-case. Unipolar signals, arising from cardiac potentials accumulated over a larger surface of the ventricle, generally contain more information than bipolar signals, providing a more reliable index for P-wave detection. On the other hand, bipolar signals offer better rejection of muscle and motion artifacts and noise, and provide the most detailed signal description of the electrophysiological state from a localized region of the ventricle. In addition, bipolar sensing may be preferable for particular patients who have far field P-waves which have a higher amplitude, in relation to other physiological and non-physiological signals, when detected on the ring electrode as compared to the tip electrode.

The signal on the lead 16 is input to two separate signal paths, one 16a for sensing ventricular signals and one 16b for sensing signals from throughout the heart to detect atrial depolarization signals. In the ventricular sensing path 16a, the signal on the lead is input to a preamplifier and attenuator circuit 19, which amplifies the electrical signal from the heart by a gain of thirty in the preferred embodiment of the invention. A control signal (not shown) from the controller 11 sets the variable attenuator in circuit 19 to attenuate or scale the input signal. The signal for the ventricular channel is input directly to an analog-to-digital converter 30.

In the atrial signal path 16b, the signal is input to a standard wide-band amplifier filter 20 which limits the signal to frequency components in a preselected range. In the preferred embodiment of the invention, passband frequencies of 0.5-100 Hz are appropriate and circuits for the standard wide-band amplifier filter 20 and a unity gain amplifier 25 are included in the sensing and polarization controller 15.

The filtered signal passes through unity gain amplifier 25 to the analog-to-digital converter 30 which digitizes the cardiac signal for sampling at 250 Hz. Circuits for the analog-to-digital converter 30 may be included in the analog-to-digital block 12. The output of the analog-to-digital converter 30 is coupled to a ventricular sense comparator 36 which determines whether the digital signal has the characteristics of an R-wave, a ventricular heartbeat. The operation of the ventricular sense comparator is standard in the art of cardiac pacing.

The P-wave detector 5 limits the frequency of the digitized cardiac signal using a line frequency filter 35. For example, the line frequency filter may attenuate signals below approximately 0.5 Hz and above about 11 Hz to remove line frequency noise at 50 Hz or 60 Hz, while retaining essentially all of the diagnostic farfield P-wave information contained in a cardiac signal. In one embodiment of the invention, the line frequency filter 35 is a digital bandpass filter with a high frequency cutoff set to the frequency of about 11 Hz.

The digital sample output of the line frequency filter 35 and the output of the ventricular sense comparator 36 are coupled to the input of a pacing and sensing controller 37, which analyzes the incoming signals, along with timers 17 (FIG. 1) coupled to the controller 11, to detect P-waves and R-waves, and to time the generation of ventricular pacing pulses, when appropriate. The detection of P-waves takes place in real time to provide for timely control of pacing and sensing.

In the preferred embodiment of the invention, the operations of the line frequency filter 35, ventricular sense comparator 36 and pacing and sensing controller 37 are performed by software within the controller 11 of FIG. 1. It is to be understood that alternative embodiments of the invention which employ dedicated circuitry to perform these operations are within the spirit and scope of the invention. The pacing and sensing controller 37 controls the performance of atrial-synchronized, ventricular-inhibited pacing (VDD pacing), in which sensing occurs in the atrium and the ventricle, and pacing occurs in the ventricle alone. The pacing and sensing controller 37 utilizes circuits which perform timing to determine when a pacing stimulation is due and circuits which detect sensed cardiac events. These circuits are standard in the art of cardiac pacing.

Figure 3:
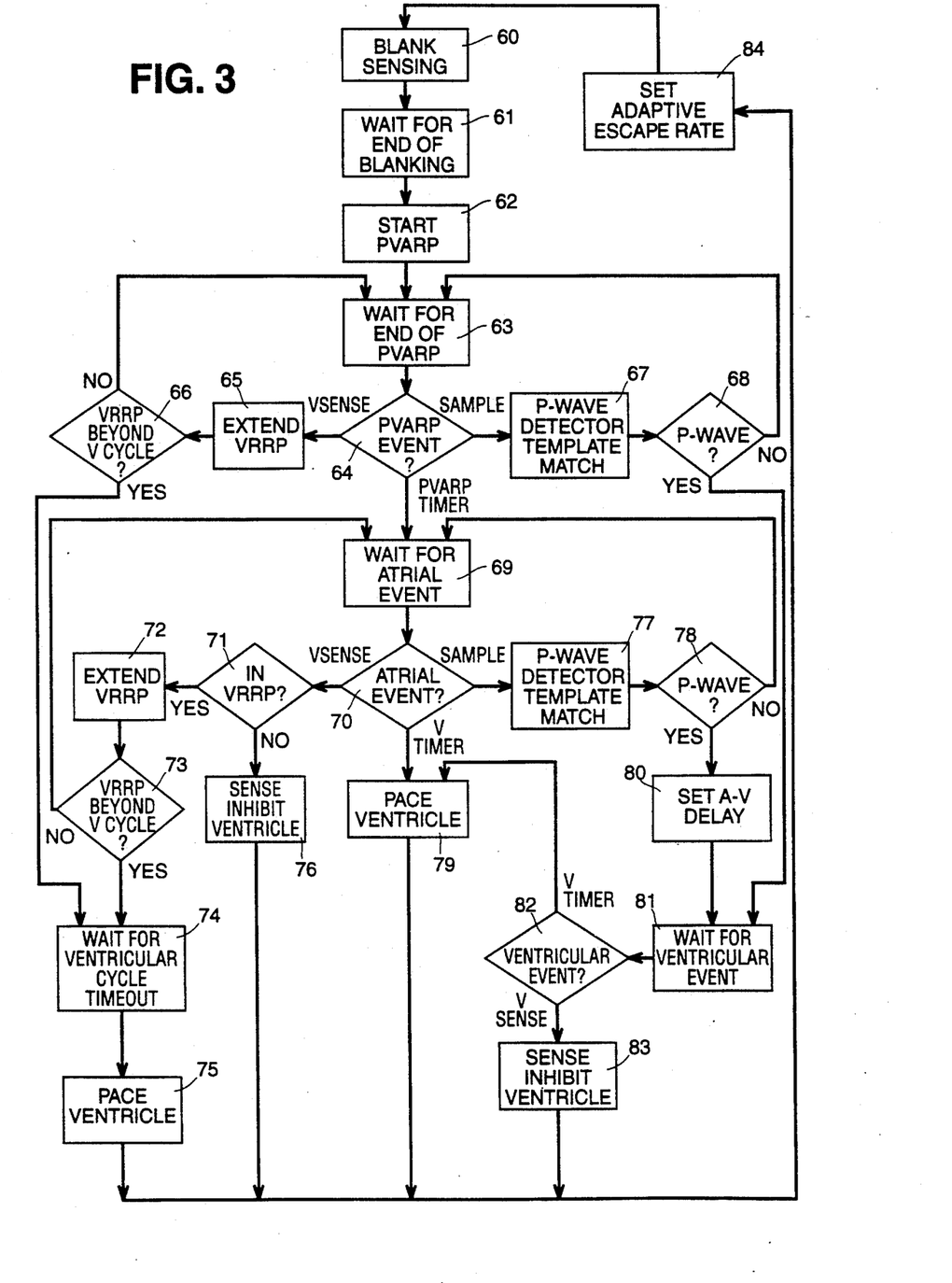
FIG. 3 is a flow diagram describing the operations of a pacing and sensing controller shown in FIG. 2.

Referring to FIG. 3, which is a flow diagram describing the operations of pacing and sensing controller 37, the pacing and sensing control procedure for VDD pacing comprises a continuous loop of subprocedures which are illustrated in blocks 60 through 83. Following the most recent ventricular sensed event or ventricular pulse generation subprocedure, the pacing and sensing controller sets a timer to measure a predetermined blanking interval and blanks all sensing from the ventricular electrode on the single ventricular lead, in blank-sensing-block 60. The blanking time duration is commonly 50 to 150 milliseconds. The blanking operation consists of disabling the sampling of signals from the digital sample stream and disabling the ventricular sense comparator wakeup input to the controller, as is common to cardiac pacemakers.

The pacing and sensing controller 37 is inactive while waiting for the end of blanking in block 61. When timeout of the blanking timer occurs, start-PVARP-block 62 prepares for sensing during the postventricular atrial refractory period (PVARP). In block 62, the pacing and sensing controller enables the ventricular sense comparator wakeup, sets the comparator threshold level to allow detection of ventricular sense events, sets a timer to a predetermined PVARP duration and enables sampling of the digital data stream for detection of P-waves. The ventricular sense comparator threshold value is set to a low level to detect noise such as myopotentials (at the end of the ventricular refractory period, the threshold is set to a higher level to better distinguish R-waves). R. H. Whigham, in U.S. Pat. No. 4,779,617, entitled "Pacemaker Noise Rejection System", issued Oct. 25, 1988, describes an apparatus and method for appropriately setting the ventricular sense comparator to distinguish noise and cardiac signals. The disclosure of said U.S. Pat. No. 4,779,617 is incorporated herein by reference. In the preferred embodiment of the present invention, the PVARP interval is programmable using telemetric communication with a default setting of about 220 ms.

The pacing and sensing controller 37 may automatically determine the timing and duration of the PVARP interval according to the recent history of P-wave timing. For example, if P-waves are occurring at a high rate, start-PVARP-block 62 may set a shorter PVARP interval following the most recent P-wave than when the P-wave rate is slow. In this manner, the pacing and sensing controller prevents wild fluctuations in pacing rate while allowing for physiological rate variations.

Start-PVARP-block 62 also initializes a ventricular relative refractory period (VRRP) interval which assists in the detection of extraneous noise (such as myopotentials), as will be discussed hereinafter in the description of blocks 65, 66, 71, 72 and 73. Start-PVARP-block 62 initializes the VRRP to a preset value, for example 100 milliseconds.

During the PVARP, the pacing and sensing controller 37 blanks atrial sensing during the R-wave when the detection of far-field P-waves is not possible. A conventional DDD or VDD pacemaker will blank sensing in the atrial channel during the PVARP interval. In contrast, the VDD pacemaker of the present invention may attempt to detect P-waves during the PVARP but, in essence, blanks the atrial signal on the ventricular channel by way of its response to a positive detection of a P-wave. Upon the detection of a P-wave during the PVARP, the VDD pacemaker temporarily disables the synchronization of atrial activity and ventricular pacing, as will be described in detail hereinafter.

In wait-for-end-of-PVARP-block 63, the pacing and sensing controller waits for one of the enabled events, ventricular sensing (V SENSE), digital data sampling (SAMPLE) or timeout of the PVARP timer (PVARP TIMER).

Upon the occurrence of SAMPLE, PVARP-event-logic- block 64 may enable the performance of the P-wave-detector-template-match-block 67, which monitors cardiac signals from the ventricular-implanted lead. In this monitoring operation, the P-wave-detector-template-match-block 67 senses natural atrial pulses (P-waves) in a sample, using one of the structure-recognition signal processing techniques described hereinafter in the discussion of FIG. 4. As controlled by P-wave-logic-block 68, if no P-wave is detected upon this sample, the pacing and sensing controller continues to wait for the end of PVARP in block 63. If a positive P-wave detection occurs during PVARP, this may indicate the occurrence of a retrograde or premature P-wave. Since abnormal P-waves may lead to the incidence of cardiac arrhythmia, the pacing and sensing controller responds to such an event by breaking the synchrony between atrial sensing and ventricular pacing, and waiting for the timeout of the preset pacing interval timer in wait-for-ventricular-event-block 81.

If the PVARP event after wait-for-end-of-PVARP-block 63 is V SENSE, the pacing and sensing controller, by way of the operation of PVARP event logic block 64, extends the VRRP time interval in block 65. The ventricular relative refractory period is the time during which the occurrence of an R-wave is not likely. Any V SENSE signal probably arises from extraneous noise. If only a few of such noise events takes place, the pacing and sensing controller 37 will ignore them. But if numerous noise events occur, making the sensing of a true R-wave questionable, the pacing and sensing controller should act in the most conservative manner by pacing the ventricle at the timeout of the ventricular cycle timer, which was preset at the end of the previous cardiac cycle (as will be described hereinafter). Extend-VRRP-time-interval-block 65 extends the VRRP by a preset interval such as 100 milliseconds. If the extended VRRP interval is thus prolonged beyond the preset ventricular cycle time, the pacing and sensing controller waits for the ventricular cycle timeout in block 74, under the control of logic block 66. Otherwise, the pacing and sensing controller continues to monitor PVARP events in block 63.

Returning to the state following wait-for-end-of-PVARP-block 63, if the PVARP timer times out, any subsequent detected P-wave is considered a true atrial heartbeat, which will trigger a ventricular event. The PVARP-event-logic-block 64 directs the pacing and sensing controller 37 to enter wait-for-atrial-event-block 69 and continue to monitor SAMPLE and V SENSE events. In addition, wait-for-atrial-event-block 69 now monitors the preset ventricular cycle timer (V TIMER).

Upon the occurrence of SAMPLE, atrial-event-logic-block 70 enables the performance of the P-wave-detector-template-match-block 77, which monitors cardiac signals in the manner of block 67. As controlled by P-wave-logic-block 78, if no P-wave is detected upon this sample, the pacing and sensing controller 37 continues to wait for an atrial event in block 69. Upon the occurrence of a P-wave, set-A-V-delay-block 80 activates a ventricular triggering process, leading to pacing in the ventricle, by starting a timer of a timing period called the A-V delay interval. Previous to block 80, pacing in the ventricle could only be generated by means of a timeout of the ventricular cycle timer, which was preset during the previous cardiac cycle. Upon the detection of a P-wave, the VDD pacemaker of the present invention performs A-V synchronous pacing by changing a timer (V TIMER) which initiates ventricular pacing relative to the time of the detected P-wave, offset by a predetermined A-V delay interval.

The pacing and sensing controller 37 then waits for a ventricular event, V SENSE or V TIMER, in block 81. If the pacemaker senses an R-wave during the A-V interval (V SENSE), ventricular-event-logic-block 82 directs the pacing and sensing controller to end the cardiac cycle in sense-inhibit-ventricle-block 83. If the A-V delay interval times out (V TIMER) before sensing an R-wave, ventricular-event-logic-block 82 directs the controller 37 to activate the generation of a pacing stimulus via a command to the sensing and polarization controller 15 of FIG. 1 in pace-ventricle-block 79.

The pacing and sensing controller 37 prepares for the next cardiac cycle in pace-ventricle-block 79 (and 75) and sense-inhibit-ventricle-block 83 (and 76) by immediately initiating the ventricular cycle timer to a desired cardiac escape interval, the desired time between a paced or sensed ventricular cardiac event and a subsequent pacing stimulus. The escape interval timer defines the longest duration between two sequential ventricular events, either natural or stimulated. If the pacing and sensing controller fails to detect a P-wave before the escape interval timer times out, or extraneous noise, such as myopotentials, disrupts atrial and/or ventricular sensing, the pacing and sensing controller 37 will command the sensing and polarization controller 15 (FIG. 1) to generate a ventricular pacing pulse when the escape interval timer times out.

When the pacing and sensing controller 37 ends a cardiac cycle by performing either pace-ventricle-block 75 or 79, or either sense-inhibit-ventricle block 76 or 83, it performs numerous standard actions such as pacing, setting timers in preparation for the next cardiac cycle, memory updating or data logging. One of these standard actions is the setting of the escape interval. The pacemaker of the present invention derives a parameter, called an adaptive escape rate, to determine a target ventricular cardiac rate which smooths rate variations caused by occasional oversensing or undersensing of P-waves by the P-wave detector 5 (FIG. 2). The adaptive escape rate, which is determined in adaptive-escape-rate-block 84, generally follows the ventricular rate of the most recent cardiac cycles. For example, the adaptive escape rate may be an average of recent ventricular rates or intervals, an average of recent rates or intervals which is shortened or lengthened by a predetermined number of timer counts, a median value of recent intervals or another standard statistical measure. The pacemaker sets the ventricular cycle timer in accordance with the adaptive escape rate to provide for ventricular rate stability.

One embodiment of the pacemaker of the present invention includes a metabolic indicator sensor, shown generally at 38 in FIG. 1, which determines an appropriate pacing rate for an exercising patient. One such metabolic indicator sensor is described in U.S. Pat. No 4,901,725, entitled "Minute Volume Rate-Responsive Pacemaker", issued to Nappholz et al. on Feb. 20, 1990, the disclosure of which is incorporated herein by reference. A VDDR pacemaker which employs the P-wave detection apparatus and method of the present invention, would determine a metabolic indicator pacing rate according to the Nappholz method in block 84 and set the escape rate and the ventricular cycle timer accordingly. If the pacemaker detects a P-wave in P-wave-detector-template-match-block 77 which indicates intrinsic atrial activity occurring at a rate faster than a predetermined maximum atrial tracking rate (for example 100 bpm), P-wave detection may become less reliable since the P-waves are more likely to occur at the same time as T-waves and the morphology of P-waves may become irregular. Furthermore, high P-wave rates may indicate the occurrence of an arrhythmia condition, e.g., the atrium is beating too fast. Under these conditions, the pacemaker will pace the ventricle at the metabolic indicator rate, asynchronously with respect to the detected P-waves. The pacemaker will not set V TIME in set-A-V-delay-block 80 and pacing of the ventricle will take place at the metabolic indicator rate in pace-ventricle-block 79 of the previous cardiac cycle. If the rate of detected P-waves does not exceed the maximum atrial tracking rate, the pacemaker will continue to pace the ventricle in synchrony with P-waves. The maximum atrial tracking rate may be set appropriately for a patient by means of telemetric communication, via set-maximum-atrial-tracking-rate-block 85 (FIG. 1) and telemetry block 14.

Another of the actions performed by the pacing and sensing controller 37 when it ends a cardiac cycle in blocks 75, 76, 79 or 83, is adaptive P-wave windowing and thresholding as shown in the flow diagram of FIG. 5 and discussed hereinafter.

Returning to the state following wait for atrial event block 69, if the atrial event is V SENSE, the atrial-event-logic-block 70 directs logic block 71 to determine whether this occurrence of V SENSE occurred within the VRRP. If not, the V SENSE event is an R-wave, rather than a noise event, and the pacing and sensing controller 37 performs the operations of sense-inhibit-ventricle-block 76 which ends the current cardiac cycle.

After wait-for-atrial-event-block 69, if the atrial event is a V SENSE which occurs within the VRRP, logic block 71 extends the VRRP time interval in block 72 in the manner of block 65. If the extended VRRP interval is advanced beyond the preset ventricular cycle time, the pacing and sensing controller 37 waits for the ventricular cycle timeout in block 74, under the control of logic block 73. Otherwise, the pacing and sensing controller continues to monitor atrial events in block 69.

In wait-for-ventricular-cycle-timeout-block 74, the pacing and sensing controller 37 waits for the V TIMER event. This timer was set to the desired escape interval at the end of the last cardiac cycle. In this instance, ventricular pacing is not synchronized to atrial activity. Since the pacing and sensing controller directs the operation of wait-for-ventricular-cycle-timeout-block 74 only in response to noise detected during the VRRP, ventricular sensing is disabled and a ventricular pacing stimulus will always end the cardiac cycle. Upon the timeout of V TIMER, the controller 37 activates the generation of a pacing stimulus via a command to the sensing and polarization controller 15 of FIG. 1 in pace ventricle block 75.

Figure 4:
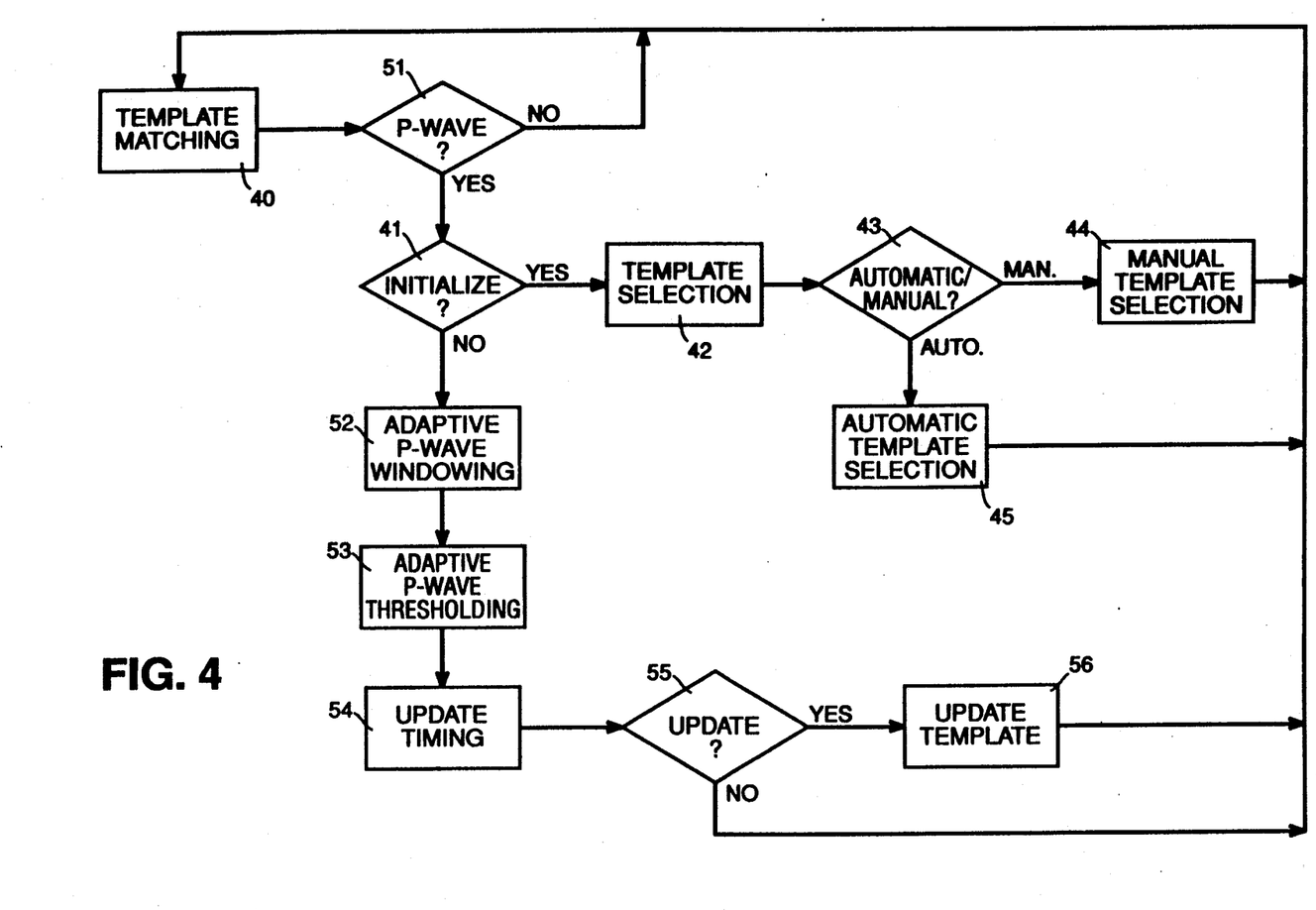
FIG. 4 is a flow diagram generally describing the operations of P-wave detector template match blocks shown in FIG. 3.

FIG. 4 is a flow diagram describing the operations of the P-wave-detector-template-match-blocks (67 and 77 of FIG. 3). Within the P-wave-detector-template-match-blocks 67 and 77, a template-matching-block 40 compares input data from the digital sample sequence to a previously stored P-wave template. Usually, the digital sample sequence is not continuous. There are gaps in the sequence corresponding to the atrial refractory period, a portion of the cardiac cycle during which the occurrence of a P-wave is not possible. The P-wave detector "windows" the input digital data sequence to prevent occurrences of "false positive" P-wave detections in which the detector perceives a P-wave when none has occurred. Adaptive- P-wave-windowing-block 52 (and block 49 of FIG. 5), which blocks are described hereinafter, define a template search window for which digital sample sequences are matched to the P-wave template. The purpose of the adaptive windowing function is to estimate within which portions of the cardiac cycle a P-wave is likely to fall. The adaptive-P-wave-windowing-blocks 49 and 52 analyze the recent history of cardiac activity with regard to the occurrences and nonoccurrences of P and R-waves and the rates of each. In general, the windowing blocks estimate where the next P-wave will occur and determine the number of samples before and after this point which should encompass the most likely period during which a P-wave will fall.

Template-matching-block 40 employs a scanning technique, in which for each sample of the digital sample sequence an operation is performed which compares each of the P-wave template samples with a corresponding sample of the digital sample sequence. In a scanning manner, the template can be considered to slide along the input signal to determine a template-matched output sequence.

It is to be understood that the scope of the present invention is to include a number of template matching signal processing techniques which include, but are not limited to, the procedures (to be defined hereinafter) of mean area of difference matching, area of difference matching, normalized mean area of difference and correlation. Other applicable procedures utilize a bin area coefficient and a mean square adaptive coefficient.

The preferred embodiment of the invention provides for usage of mean area of difference (MAD) template matching in template-matching-block 40. The MAD template matching technique determines the geometric mean of the difference between the template and signal, but normalizes this area of difference for baseline differences between the signal and the template. Equation (1) relates the procedure for performing the MAD template matching operation:

$$y_{MADi} = \frac{\sum_{j=0}^{N-1} |(t_j - \mu_T) - (s_{i+j} - \mu_s)|}{\sum_{j=0}^{N-1} |t_j - \mu_T|}, \quad (1)$$

where $y_{MADi}$ is a template matching coefficient (for location i), N is the number of data points in the template, $t_j$ is a template data point at a location j of the template memory array, $\mu_T$ is the average of all data points within the template, $s_{i+j}$ is an input signal data point at a location j offset from location i of the input signal and $\mu_s$ is the local average of N input signal data points, commencing with the input signal data point at location i. The mean signal amplitude, $\mu_s$, is calculated for each $y_{MAD}$ data point determination. Possible results of equation (1), like equations (3) and (5) described hereinafter, range from 0 to infinity. If the signal sequence identically matches the template sequence, the result of equation (1) is zero. For larger degrees of variation between the signal sequence and the template, the equation result becomes larger. The invention's preferred embodiment employs the MAD template matching procedure because, in preliminary clinical investigations, MAD was the most accurate method for detecting P-waves.

In practice, to provide for P-wave detection, template-matching-block 40 performs the operation of equation (1) by substituting an adaptive threshold value, $\gamma$, for the template matching coefficient $y_{MAD}$ and performing comparison of inequality (2):

$$\gamma \sum_{j=0}^{N-1} |t_j - \mu_T| > \sum_{j=0}^{N-1} |(t_j - \mu_T) - (s_{i+j} - \mu_s)|. \quad (2)$$

If the result of this inequality is true, then a P-wave has been detected

Whenever the P-wave detector 5 changes either the threshold, $\gamma$, in block 53 (or in block 50 of FIG. 5) or the template in blocks 44, 45 and 56, it updates and stores the standard for P-wave comparison, given by the left side of inequality (2). The P-wave detector stores this standard for P-wave comparison as a single-quantity value in a memory location and later accesses this memory location for the purposes of template matching for P-wave detection. When the P-wave detector changes the template in blocks 44, 45 and 56, it updates and stores an array of template samples, each of which is offset by the average template value, $\mu_T$.

Another embodiment of the present invention employs an area of difference (AD) matching procedure in template-matching-block 40. Equation (3) relates the procedure for performing the AD template matching operation:

$$y_{ADi} = \frac{\sum_{j=0}^{N-1} |t_j - s_{i+j}|}{\sum_{j=0}^{N-1} |t_j|}, \quad (3)$$

where $y_{ADi}$ is a template matching coefficient (for location i), N is the number of data points in the template, $t_j$ is a template data point at a location j of the template memory array and $s_{i+j}$ is an input signal data point at a location j offset from location i of the input signal.

A still further embodiment of the present invention may employ a correlation matching procedure in template-matching-block 40. Equation (4) relates the procedure for performing the correlation template matching operation:

$$\rho_i = \frac{\sum_{j=0}^{N-1} (t_j - \mu_T)(s_{i+j} - \mu_s)}{\sqrt{\sum_{j=0}^{N-1}(t_j - \mu_T)^2 \sum_{j=0}^{N-1}(s_{i+j} - \mu_s)^2}}, \quad (4)$$

where p is a correlation coefficient (for location i), N is the number of data points in the template, $t_j$ is a template data point at a location j of the template memory array, $\mu_T$ is the average of all data points within the template, $s_{i+j}$ is an input signal data point at a location j offset from location i of the input signal and $\mu_s$ is the local average of N input signal data points, commencing with the input signal data point at location i. The result of equation (4), unlike that of equations (1), (3) and (5), ranges in value from 1 to $-1$, with a perfect match of the signal to the template yielding a result of 1.

Another embodiment of the present invention may employ a normalized mean area of difference (NMAD) template matching procedure in template-matching-block 40. Equation (5) designates the procedure for performing the (NMAD) template matching operation:

$$y_{NMADi} = \sum_{j=0}^{N-1} \left| \frac{t_j - \mu_T}{\sum_{k=0}^{N-1} |t_k - \mu_T|} - \frac{s_{i+j} - \mu_s}{\sum_{k=0}^{N-1} |s_k - \mu_T|} \right|, \quad (5)$$

where $y_{NMADi}$ is a template matching coefficient (for location i), N is the number of data points in the template, $t_j$ is a template data point at a location j of the template memory array, $\mu_T$ is the average of all data points within the template, $s_{i+j}$ is an input signal data point at a location j offset from location i of the input signal and $\mu_s$ is the local average of N input signal data points, commencing with the input signal data point at location i.

Depending on the result of the template matching operation of block 40, P-wave-logic-block 51 controls whether the P-wave detector template match continues to sample or processes the detected P-wave. If the template-matching-block 40 does not detect a P-wave, the template-matching-block 40 continues to sample the incoming digital signal. Otherwise, control of the procedure progresses to initialize-logic-block 41.

Initialize-logic-block 41 of FIG. 4 determines whether to initialize or select a new template waveform, on one hand, or to detect P-waves, on the other hand. Initialize-logic-block 41 activates template selection block 42 to perform template selection according to one of two procedures, one manual, in block 44, the other automatic, in block 45. A telemetric command from an associated external programming device determines which of the two procedures will be utilized by preconditioning an automatic/manual-logic-block 43.

During the manual template selection procedure of block 44, the P-wave detector 5 senses and digitizes intracardiac electrogram data (ICEG) and transmits these electrograms to the external programming device. The P-wave detector may also, concurrent with the transmission of ICEG signals, transmit timing markers designating the identity and time of sensed cardiac signals, either natural or stimulated. ICEG sensing and digitizing, cardiac events sensing, pacing stimulation and transmission of ICEG and cardiac event sensed signals are all standard in the art of cardiac pacemakers. Concurrently with these actions by the P-wave detector, the external programming device receives the digitized ICEG signals and cardiac event markers and stores this information in a memory. Upon the reception of an event marker, the external programming device may stop storing ICEG samples and display a sequence of samples on a video screen so that the samples preceding the R-wave remain in memory. For example, the device may store and display the intracardiac electrogram signals acquired during 300 ms preceding and 100 ms following R-wave detection. An operator of the external programming device may visually detect a P-wave in the display. If no P-wave appears in the display, the operator may restart the P-wave monitoring and sampling procedure until a P-wave does appear in the display. Using cursors associated with the video screen of the external programming device, the operator may provide alignment markers which designate particular points in the ICEG signal. For example, the P-wave position, relative to the R-wave, may be determined by visually detecting the P-wave and positioning two cursors, one at the P-wave onset and one designating the P-wave offset. Alternatively, one cursor may designate the P-wave onset with offset determined by the preset fixed template length. According to the position of these alignment markers, the operator may save a selected sequence of samples of the waveform in a memory, either by storing the waveform segment in a template memory or by averaging the waveform segment into previously acquired waveform segments. In this manner, the operator may save a particular waveform segment template which is representative of P-wave waveforms, or may average a number of representative P-wave segments. The operator may subsequently control the external programming device to transmit the acquired template into the internal memory (within the Controller 11 of FIG. 1), which is used by the implanted P-wave detector 5.

In the automatic template selection procedure of block 45, a preliminary template, which has a predetermined signal morphology that is characteristic of an average P-wave, has been previously stored in memory. In template-matching-block 40, the P-wave detector 5 has previously performed template matching of data samples with the preliminary P-wave. If the result of the template matching procedure meets the requirements of a predefined criteria, for example the result of the aforementioned inequality (2) is true, a P-wave is deemed to have taken place. When a P-wave has been detected, the P-wave detector 5 determines an appropriate starting sample location for the template The automatic-template-selection-block 45 may use the positioning of an R-wave signal, if any, with respect to the P-wave, to set the template starting location If the timing of P-wave events is in synchrony with R-wave events, over a number of cardiac cycles, the automatic-template-selection-block 45 may localize samples of the template according to R-wave timing markers to more accurately place P-wave samples within the template.

The P-wave detector 5 analyzes the results of the previously discussed template matching operation to determine the location of a P-wave. The template matching operation was performed in block 40 for each sample point in the waveform memory. Each template matching operation, as defined by an appropriate aforesaid equation (1) and (3) through (5), yields a single template matching result. The result which indicates the most similarity between the predetermined preliminary P-wave template and the sampled data, designates a marker which determines the P-wave location for a cardiac cycle. Based on the sample location of this marker, the P-wave detector stores a preset number of P-wave template samples, starting at the marker location or starting a predetermined number of samples preceding or succeeding the marker location. For the initial sample of template selection, the P-wave detector may store the acquired P-wave template in a memory without modification and, for subsequent samples, the detector may average acquired sequences for each cardiac cycle into the template built from data acquired in previous cycles. The P-wave template length is programmable with a default duration of 100 ms. If the template matching method does not yield a result consistent with detection of a P-wave, no sampled data is stored for a cardiac cycle The automatic template selection procedure of block 45 continues to acquire P-wave waveform data and to develop the P-wave template for a predetermined number of sampled cardiac cycles.

When initialization is not selected, initialize- logic-block 41 provides for the P-wave-logic-block 51 to pass control to adaptive-P-wave-windowing-block 52. With respect to the discussion of adaptive-P-wave-windowing and -thresholding-blocks 52 and 53, it is instructive to first discuss similar operations which take place upon the detection of an R-wave rather than a P-wave. Referring to FIG. 5, the pacing and sensing controller 37 of FIG. 2 performs the R-wave detect operation of block 47 in response to the generation of a ventricular pacing stimulus or the sensing of an R-wave. This procedure is accessed at the end of the cardiac cycle by the pace-ventricle-blocks 75 and 79 and the sense-inhibit-ventricle-blocks 76 and 83 of FIG. 3.

R-wave-detect-block 47 determines whether two consecutive R-waves have occurred without the detection of an intervening P-wave. R-wave-detect-block 47 then directs control of the method to consecutive-R-waves-logic-block 48.

If the P-wave detector 5 does not detect a P-wave in the time between two consecutive R-waves, upon the occurrence of the latter R-wave the consecutive-R-waves-logic-block 48 directs the controller to perform adaptive P-wave windowing and thresholding in blocks 49 and 50. Consecutive-R-waves-logic-block 48 only allows the controller to perform adaptive P-wave windowing and thresholding if the function is enabled via programming. If the detected R-wave follows a previous P-wave or the windowing and thresholding function is not enabled, the consecutive-R-waves-logic-block 48 steers the P-wave detector operations to return to the template-matching-block 40 to analyze data for the next cardiac cycle.

Adaptive-P-wave-windowing-block 49 adjusts the search window which defines whether template-matching-block 40 performs matching on a particular digital sample or sample sequence. To reach block 49, consecutive R-wave events must have occurred With no intervening P-wave Either the P-wave detector 5 has missed a P-wave event or a premature contraction in the ventricle has taken place that is out of sequence with the heart's normal intrinsic rhythm. In either case, the location of a P-wave in the next cardiac cycle is more difficult to predict so adaptive-P-wave-windowing-block 49 increases the size of the template search window After performing adaptive windowing, the P-wave detectors performs adaptive P-wave thresholding at block 50. The purpose of thresholding is to modify the matching coefficient threshold to allow for short-term changes in P-wave morphology. The action of adaptive-P-wave-thresholding-block 50 depends on whether the P-wave detector has missed a P-wave event or a premature ventricular contraction (PVC) has occurred.

In the case of a missed P-wave, indicating short-term changes in P-wave morphology, the adaptive-P-wave-thresholding-block 50 modifies the matching coefficient threshold. In the preferred embodiment of the invention, which uses the mean area of difference (MAD) method of template matching, the matching coefficient threshold is initially set to 0.30. Since a P-wave did not occur within a cardiac cycle, defined as the time between two R-waves, the controller 37 performs the procedure of adaptive-P-wave-thresholding-block 50, which increments the matching coefficient threshold. For example, adaptive P-wave thresholding may increase the matching coefficient threshold by increments of 0.05 until a cardiac cycle occurs within which a P-wave is detected or until the coefficient reaches a minimum of 0.60.

The adaptive-P-wave-thresholding-block 50 determines whether a PVC has occurred by analyzing the time intervals between the previous two consecutive R-wave events in comparison to a normal or average interval for recent such events. For example, if the current R-wave to R-wave interval is less than a predetermined fraction (e.g. 80%) of the previous R-to-R interval, or a fraction of an average of the last few intervals, the adaptive-P-wave-thresholding-block 50 assumes the occurrence of a PVC. In the case of a PVC event, the adaptive-P-wave-thresholding-block 50 may modify the matching coefficient threshold by a smaller amount or leave the threshold unchanged, as is desired for the preferred embodiment of the invention.

Figure 5:
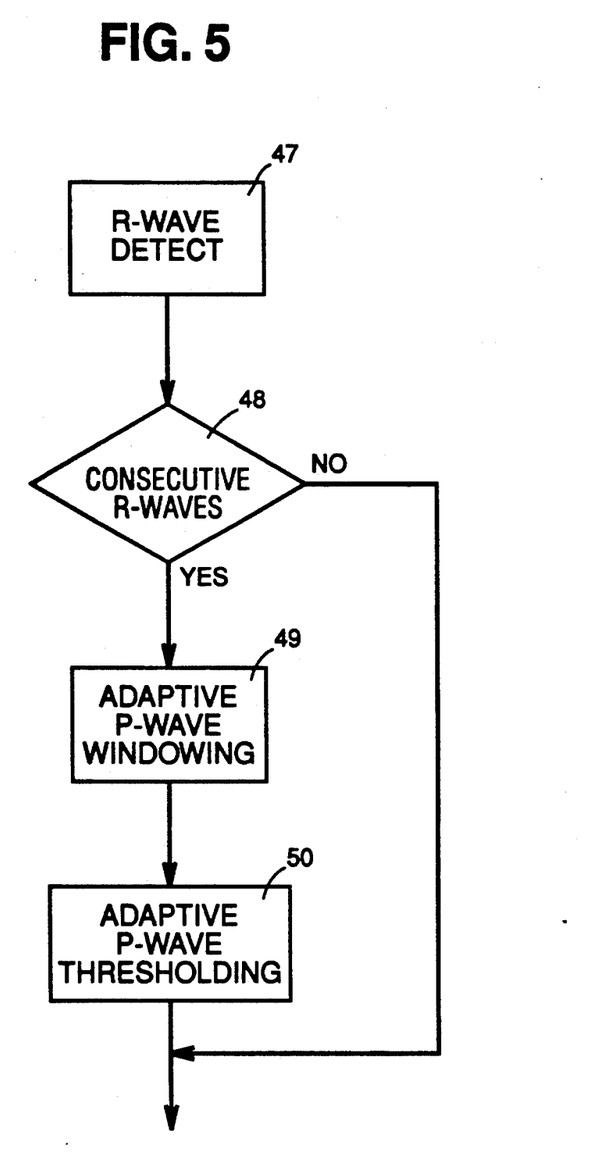
FIG. 5 is a flow diagram of an R-wave detection procedure performed at the end of each cardiac cycle by operations of the pacing and sensing controller of FIG. 2.

Again referring to FIG. 4, the P-wave detector's template matching procedures shown there also perform adaptive P-wave windowing and thresholding Adaptive-P-wave-windowing-block 52 performs an operation which is complementary to the function of block 49 of FIG. 5. Block 49 expanded the duration of the threshold search window because the detection of consecutive R-wave events with no intervening P-wave event made the expected timing of the next P-wave less predictable. Adaptive-P-wave-windowing-block 52, in response to the detection of regularly occurring P-waves, may shorten the duration of the threshold search window under certain predefined circumstances. For example, when P-waves have consistently fallen within a particular portion of the search window for a number of the most recent cardiac cycles, block 52 may decrease the threshold search window duration. Furthermore, if the time that P-waves occur within the search window changes over time, block 52 may alter the "centering" of the application of the window by shifting the time of sampling in relationship to events within the cardiac cycle in template-matching-block 40.

In a manner similar to that of complementary adaptive-P-wave-windowing-blocks 49 and 52, adaptive-P-wave-thresholding-blocks 50 (FIG. 5) and 53 (FIG. 4) control the value of the threshold matching coefficient. Adaptive-P-wave-thresholding-block 53 performs an operation which is complementary to the adaptive-P-wave-thresholding-operation of block 50. While block 50 increases the threshold matching coefficient to a maximum, adaptive-P-wave-thresholding-block 53 sets a minimum threshold value. Adaptive-P-wave-thresholding-block 53 counts the consecutive number of cardiac cycles within which P-waves are detected. If the count exceeds a predetermined number, for example four cardiac cycles, then adaptive-P-wave-thresholding-block 53 may determine a new threshold matching coefficient. For example, a new threshold may be set to a preset factor (for example 1.25) multiplied by the minimum matching coefficient which was determined in each cardiac cycle, averaged over the past four cardiac cycles.

Periodically, the P-wave detector's template matching procedure updates the P-wave template. Update-timing-block 54 either counts the number of detected P-waves or times a predetermined time duration since the last P-wave template updating operation to determine whether to update the template or to simply detect P-waves. For example, the template may be updated upon the detection of every hundredth P-wave or every five minutes. Update-logic-block 55 controls whether the P-wave detector's template matching procedure updates the template according to the determination of update-timing-block 54. When update-logic-block 55 activates update-template-block-56, the P-wave detector's template matching procedure aligns the location of the P-wave within the current sample with a similar location within the template samples.

Within update-template-block 56, the P-wave detector's template matching procedure evaluates the results of the template matching operation for each sample to determine the location of a P-wave. The result corresponding to the sample location which indicates the most similarity between the predetermined preliminary P-wave template and the sampled data designates a marker for the P-wave location Update- template-block 56 may update the P-wave template using an averaging technique for combining the current sequence into the existing P-wave template. The preferred embodiment of the P-wave detector's template matching procedure updates the template by increasing or decreasing each template sample by a count of one, depending on whether the corresponding sample within the current sequence is greater than or less than the template sample. If the sample within the current sequence is the same as the template sample, the template sample remains unchanged. Other averaging techniques may include weighted running averaging, or simply replacing the current template sequence with a newly acquired sequence.

For most cardiac cycles, update-logic-block 55 directs the P-wave detector's template matching procedure to detect P-waves or R-waves, rather than to update the P-wave template.

Following completion of the procedures of any of the template-selection-blocks 44 and 45, adaptive-P-wave-thresholding-block 50, update-logic-block 55 or update-template-block 56, the P-wave detector's template matching operations return to the template-matching-block 40 to analyze data for the next cardiac cycle.

It is evident from the foregoing that the present invention, by performing efficient signal analysis of cardiac signals to detect remote depolarizations of heart tissue, provides the advantages of dual-chamber pacing in a pacemaker which requires the implantation of only a single standard lead within the heart.

Although the invention has been described with reference to a particular embodiment, it is to be understood that this embodiment is merely illustrative of the application of the principles of the invention. Hence numerous modifications may be made therein and other arrangements may be devised without departing from the spirit and scope of the invention.

We claim:

1. A cardiac stimulating apparatus for implantation in a patient, comprising:
   a first electrode for implantation in the patient's body other than in the patient's atrium;
   a second electrode for implantation in the patient's ventricle and adapted for interengagement and electrical coupling with tissue of the patient's ventricle;
   means, coupled to said electrodes, for generating and transmitting stimulation pulses through said second electrode to the tissue of the ventricle;
   means, coupled to said electrodes, for sensing from the tissue of the patient's ventricle intrinsic cardiac electrical energy in such tissue and detecting therefrom the occurrence of P-waves; and
   control means, having timing means therein, for controlling said generating and transmitting means to provide a stimulation pulse to said second electrode for provision to the tissue of the ventricle, in response to said sensing means detecting the occurrence of a P-wave in the intrinsic electrical activity in the tissue of the patient's ventricle.

2. An apparatus according to claim 1, further including a bipolar pacing leading having tip and ring electrodes, and wherein:
   said first and second electrodes each comprise a separate one of the tip and ring electrodes of said bipolar pacing lead.

3. An apparatus according to claim 1, wherein:
   said apparatus includes an external case, nd
   said first electrode in the external case of said apparatus.

4. An apparatus according to claim 1, wherein:

said timing means times a predetermined delay following the detection of an occurrence of a P-wave and then enables said control means to control said generating and transmitting means to provide a stimulation pulse to said second electrode.

5. A cardiac stimulating apparatus for implantation in a patient, comprising:
a first electrode for implantation in the patient's body other than in the patient's atrium;
a second electrode for implantation in the patient's ventricle and adapted for interengagement and electrical coupling with tissue of the patient's ventricle;
means, coupled to said electrodes, for generating and transmitting stimulation pulses through said second electrode to the tissue of the ventricle;
means, coupled to said electrodes, for sensing from the tissue of the patient's ventricle intrinsic cardiac electrical activity in such tissue and detecting therefrom the occurrence of P-waves;
means responsive to said intrinsic cardiac activity sensing means for deriving an indication of an intrinsic atrial heartbeat rate;
means for establishing a predetermined maximum atrial heartbeat rate;
means for determining a metabolic indicator heartbeat rate;
means for comparing said indication of intrinsic atrial heartbeat rate to said predetermined maximum atrial heartbeat rate and to said metabolic indicator rate; and
control means responsive to said comparing means and including timing means therein for controlling said generating and transmitting means to stimulate any electrically coupled ventricle tissue based on the timing of the occurrence of at least one P-wave when said intrinsic atrial heartbeat rate indication is slower than said predetermined maximum atrial heartbeat rate, and for controlling said generating and transmitting means to stimulate any electrically coupled ventricle tissue based on said metabolic indicator heartbeat rate when said intrinsic atrial heartbeat rate exceeds said predetermined maximum atrial heartbeat rate.

6. An apparatus according to claim 5, wherein:
said sensing and detecting means further comprises:
means for producing a time sequence of waveform segment template samples characterizing a P-wave;
means for receiving and for storing waveform segment templates which are representative of P-wave waveforms;
means for producing a time sequence of intrinsic cardiac electrical unknown signal samples from said time sequence of waveform segment template samples to derive a template matching coefficient;
means for receiving and storing predetermined threshold criteria;
means for comparing said derived template matching coefficient with said threshold criteria; and
means for classifying said unknown signal samples as a P-wave when said template matching coefficient exceeds said threshold criteria.

7. An apparatus according to claim 6, wherein:
said timing means times a predetermined delay following the detection of an occurrence of a P-wave and then enables said control means to control said generating and transmitting means to provide a stimulation pulse to said second electrode.

8. An apparatus according to claim 6, further including a bipolar pacing leading having tip and ring electrodes therein, and wherein:
said first and second electrodes each comprise a separate one of the tip and ring electrodes of said bipolar pacing lead.

9. An apparatus according to claim 6 wherein:
said matching means derives said template matching coefficient by performing a template matching operation selected from a group of operations consisting of:
determining an area of difference,
determining a mean area of difference,
determining a normalized mean area of difference,
determining a correlation coefficient,
determining a bin area coefficient, and
determining a least mean square adaptive coefficient.

10. A method of providing heart stimulating therapy to a patient's heart, comprising:
sensing and sampling intrinsic cardiac electrical signals in the ventricle of the patient's heart;
detecting the occurrence of P-waves form said intrinsic ventricular electrical signal samples;
determining the time of occurrence of at least one P-wave;
deriving pulse generation control signals based on the occurrence of said P-wave;
generating stimulation pulses in response to said pulse generation control signals and providing said pulses to said ventricle.

11. A method according to claim 10, wherein:
said step of deriving pulse generation control signals comprises the substeps of:
sensing intrinsic ventricular electrical signals following the occurrence of a P-wave in the atrium of the patient's heart;
characterizing and storing said ventricular electrical signals sensed following the occurrence of a P-wave in a time sequence of template samples;
subsequently monitoring a time sequence of intrinsic ventricular electrical signal samples when intrinsic atrial electrical activity is unknown;
matching said monitored sample with said stored template samples to derive a template matching coefficient;
providing a template matching coefficient threshold value;
comparing said template matching coefficient with said threshold value; and
classifying said monitored sample as a P-wave when said template matching coefficient is greater than said threshold value.

12. A method according to claim 11, wherein:
upon the classifying of said monitored samples as a P-wave, enabling a predetermined delay, and thereafter enabling said pulse generation step.

13. A cardiac stimulating apparatus for implantation in a patient, comprising:
a first electrode for implantation in the patient's body other than in the patient's atrium;
a second electrode for implantation in the patient's ventricle and adapted for interengagement and electrical coupling with tissue of the patient's ventricle;
means, coupled to said electrodes, for generating and transmitting stimulation pulses through said second electrode to the tissue of the ventricle;

means, coupled to said electrodes, for sensing from the tissue of the patient's ventricle intrinsic cardiac electrical activity in such tissue and detecting therefrom the occurrence of P-waves, said sensing and detecting means further comprising:

means for producing a time sequence of waveform segment template samples characterizing a P-wave, means for receiving and for storing waveform segment templates which are representative a P-wave waveforms, means for producing a time sequence of intrinsic cardiac electrical unknown signal samples from said second electrode, means for matching said unknown signal samples to said time sequence of waveform segment template samples to derive a template matching coefficient, means for receiving and storing predetermined threshold criteria, means for comparing said derived template matching coefficient with said threshold criteria, and means for classifying said unknown signal samples as a P-wave when said template matching coefficient exceeds said threshold criteria, said apparatus further comprising:

control means, having timing means therein, for controlling said generating and transmitting means to provide a stimulation pulse to said second electrode for provision to the tissue of the ventricle, in response to said sensing means detecting the occurrence of a P-wave in the intrinsic electrical activity in the tissue of the patient's ventricle.

14. An apparatus according to claim 12, wherein:

said matching means derives said template matching coefficient by performing a template matching operation selected from a group of operations consisting of:
 determining an area of difference,
 determining a mean area of difference,
 determining a normalized mean area of difference,
 determining a correlation coefficient,
 determining a bin area coefficient, and
 determining a least mean square adaptive coefficient.

15. An apparatus according to claim 13, wherein:

said timing means times a predetermined delay following the detection of an occurrence of a P-wave and then enables said control means to control said generating and transmitting means to provide a stimulation pulse to said second electrode.

16. An apparatus according to claim 13, further including a bipolar pacing leading having tip and ring electrodes, and wherein:

said first and second electrodes each comprise a separate one of the tip and ring electrodes of said bipolar pacing lead.

17. An apparatus according to claim 16, wherein:

said matching means derives said template matching coefficient by performing a template matching operation selected from a group of operations consisting of:
 determining an area of difference,
 determining a mean area of difference,
 determining a normalized mean area of difference,
 determining a correlation coefficient,
 determining a bin area coefficient, and
 determining a least mean square adaptive coefficient.

18. An apparatus according to claim 16, wherein:

said timing means times a predetermined delay following the detection of an occurrence of a P-wave and then enables said control means to control said generating an transmitting means to provide a stimulation pulse to said second electrode.

19. A cardiac stimulating apparatus for implantation in a patient, comprising:

a bipolar pacing lead having tip and ring electrodes therein;

a first electrode for implantation in the patient's body other than in the patient's atrium;

a second electrode for implantation in the patient's ventricle and adapted for interengagement and electrical coupling with tissue of the patient's ventricle;

a first and second electrode each comprising a separate one of the tip and ring electrodes of said bipolar pacing lead;

means, coupled to said electrodes, for generating and transmitting stimulation pulses through said second electrode to the tissue of the ventricle;

means, coupled to said electrodes, for sensing from the tissue of the patient's ventricle intrinsic cardiac electrical activity in such tissue and detecting therefrom the occurrence of P-waves;

means responsive to said intrinsic cardiac activity sensing means for deriving an indication of an intrinsic atrial heartbeat rate;

means for establishing a predetermined maximum atrial heartbeat rate;

means for determining a metabolic indicator heartbeat rate;

means for comparing said indication of intrinsic atrial heartbeat rate to said predetermined maximum atrial heartbeat rate and to said metabolic indicator rate; and control means responsive to said comparing means and including timing means therein for controlling said generating and transmitting means to stimulate any electrically coupled ventricle tissue based on the timing of the occurrence of at least one P-wave when said intrinsic atrial heartbeat rate indication is slower than said predetermined maximum atrial heartbeat rate, and for controlling said generating and transmitting means to stimulate any electrically coupled ventricle tissue based on said metabolic indicator heartbeat rate when said intrinsic atrial heartbeat rate exceeds said predetermined maximum atrial heartbeat rate.

20. An apparatus according to claim 19, wherein:

said timing means times a predetermined delay following the detection of an occurrence of a P-wave and then enables said control means to control said generating and transmitting means to provide a stimulation pulse to said second electrode.

21. A cardiac stimulating apparatus for implantation in a patient, comprising:

a first electrode for implantation in the patient's body other than in the patient's atrium;

a second electrode for implantation in the patient's ventricle and adapted for interengagement and electrical coupling with tissue of the patient's ventricle;

means, coupled to said electrodes, for generating and transmitting stimulation pulses through said second electrode to the tissue of the ventricle;

means, coupled to said electrodes, for sensing from the tissue of the patient's ventricle intrinsic cardiac electrical activity in such tissue and detecting therefrom the occurrence of P-waves;

means responsive to said intrinsic cardiac activity sensing means for deriving an indication of an intrinsic atrial heartbeat rate;

means for establishing a predetermined maximum atrial heartbeat rate;

means for determining a metabolic indicator heartbeat rate;

means for comparing said indication of intrinsic atrial heartbeat rate to said predetermined maximum atrial heartbeat rate and to said metabolic indicator rate; and control means responsive to said comparing means and including timing means therein for controlling said generating and transmitting means to stimulate any electrically coupled ventricle tissue based on the timing of the occurrence of at least one P-wave when said intrinsic atrial heartbeat rate indication is slower than said predetermined maximum atrial heartbeat rate, and for controlling said generating and transmitting means to stimulate any electrically coupled ventricle tissue based on said metabolic indicator heartbeat rate when said intrinsic atrial heartbeat rate exceeds said predetermined maximum atrial heartbeat rate, said timing means timing a predetermined delay following the detection of an occurrence of a P-wave and then enabling said control means to control said generating and transmitting means to provide a stimulation pulse to said second electrode.

* * * * *